United States Patent
Saebo et al.

(10) Patent No.: US 7,078,051 B1
(45) Date of Patent: Jul. 18, 2006

(54) CONJUGATED LINOLEIC ACID ALKYL ESTERS IN FEEDSTUFFS AND FOOD

(75) Inventors: Asgeir Saebo, Oersta (NO); Carl Skarie, Detroit Lakes, MN (US)

(73) Assignee: Natural Asa (NO)

(*) Notice: Subject to any disclaimer, the term of this patent is extended or adjusted under 35 U.S.C. 154(b) by 0 days.

(21) Appl. No.: 09/132,593

(22) Filed: Aug. 11, 1998

(51) Int. Cl.
A61K 47/00 (2006.01)
A61K 31/20 (2006.01)

(52) U.S. Cl. ............... 424/439; 514/560; 514/558

(58) Field of Classification Search ............ 424/439; 514/558, 560
See application file for complete search history.

(56) References Cited

U.S. PATENT DOCUMENTS

| | | | |
|---|---|---|---|
| 2,242,230 A | 5/1941 | Burr | 260/398 |
| 2,350,583 A | 6/1944 | Bradley | 260/105.6 |
| 3,162,658 A | 12/1964 | Baltes et al. | 260/405.6 |
| 3,278,567 A | 10/1966 | Rathjen et al. | 260/405.6 |
| 3,729,379 A | 4/1973 | Emken | 195/30 |
| 4,164,505 A | 8/1979 | Krajca | 260/418 |
| 4,381,264 A | 4/1983 | Struve | 260/405.6 |
| 5,208,356 A | 5/1993 | Pariza et al. | 554/79 |
| 5,428,072 A * | 6/1995 | Cook et al. | 514/560 |
| 5,430,066 A | 7/1995 | Cook et al. | 514/560 |
| 5,554,646 A * | 9/1996 | Cook et al. | 514/560 |
| 5,585,400 A | 12/1996 | Cook et al. | 514/560 |
| 5,674,901 A | 10/1997 | Cook et al. | 514/558 |
| 5,760,082 A | 6/1998 | Cook et al. | 514/560 |
| 5,804,210 A | 9/1998 | Cook et al. | 424/440 |
| 5,814,663 A | 9/1998 | Cook et al. | 514/560 |
| 5,827,885 A | 10/1998 | Cook et al. | 514/558 |
| 5,851,572 A | 12/1998 | Cook et al. | 426/2 |
| 5,855,917 A | 1/1999 | Cook et al. | 424/502 |
| 5,856,149 A | 1/1999 | Pariza et al. | 435/134 |
| 5,986,116 A | 11/1999 | Iwata et al. | 554/126 |
| 6,015,833 A * | 1/2000 | Sabo et al. | 514/558 |
| 6,160,140 A | 12/2000 | Bhaggan et al. | 554/126 |
| 6,184,009 B1 | 2/2001 | Cain et al. | 435/134 |

FOREIGN PATENT DOCUMENTS

| | | |
|---|---|---|
| EP | 440325 | 7/1991 |
| EP | 779033 A1 | 6/1997 |
| EP | 839897 | 6/1998 |
| EP | 902082 | 3/1999 |
| EP | 0950410 | 12/2000 |
| GB | 558881 | 1/1944 |
| WO | WO 97/18320 | 5/1997 |
| WO | WO 97/46230 | 12/1997 |
| WO | WO 98/05318 | 2/1998 |
| WO | WO 98/49129 | 11/1998 |

(Continued)

OTHER PUBLICATIONS

Klein and Crauer, *JAOCS* 51: 382A–385A (1971).

(Continued)

*Primary Examiner*—Shengjun Wang
(74) *Attorney, Agent, or Firm*—Medlen & Carroll, LLP

(57) ABSTRACT

A novel method of delivering conjugated linoleic acid to an animal involves compounding feed or food for human consumption with a biologically active amount of conjugated linoleic acid alkyl ester (CLA-ester). The CLA-ester comprises a mixture of c9,t11-octadecanoic acid and t10, c12-octadecanoic acid, with contaminating isomers being present at an aggregate percentage of less than 5. Manufactured from sunflower or safflower oil, the CLA-esters contain less than 0.5 percent phosphatidyl residue, so that a food grade product is made without special purification and refining steps.

7 Claims, 2 Drawing Sheets

FOREIGN PATENT DOCUMENTS

| WO | WO 01/44485 A | 7/2001 |
|---|---|---|
| WO | WO 01/53512 A | 7/2001 |

OTHER PUBLICATIONS

Burkhardt, *JAOCS* 48: 697-699 (1971).
Birt et al., *Cancer Res.*, 52: 2035s (1992).
Ha, et al., *Cancer Res.*, 50: 1097 (1990).
Cowan, *JAOCS*, 72: 492 (1950).
Kass, et al., *J. Am. Chem. Soc.*, 61: 4829 (1939).
Radlove, et al., *Ind. Eng. Chem.*, 38: 997 (1946).
Sullivan, *J. Am. Oil Chemists' Soc.*, 53: 359 (1976).
Scholfield and Koritalia, "A Simple Method for Preparation of Methyl trans-10,cis-12 Octadecadienoate," *JAOCS* 47(8): 303 (1970).
Sugano et al., "Conjugated Linoleic Acid Modulates Tissue Levels of Chemical Mediators and Immunoglobulins in Rats," *Lipids*, 33(5):521-27 (1998).
Maltreya Catalog, 1997, pp. 33-34.
Hudtwalcker & Co. AS Technical Data Sheet, exact publication date unknown.
Selin CLA Product Literature, Jan. 1997.
Lipid Technology Newsletter, Peter J. Barnes, Ed., vol. 4, No. 5, pp. 85-86 (Oct. 1998).
Natural Lipids Ltd. AS Technical Data Sheet, Jan. 20, 1997, describes CLA compositions with varying amounts of CLA.
Ron Udell, Information About Conjugated Linoleic Acid, published by Soft Gel Technologies Incorporated, exact publication date unknown.
Belury, "Conjugated dienoic linoleate: a polyunsaturated fatty acid with unique chemoprotective properties," *Nutr. Rev.* 53: 83-9 (1995).
Handbook of Soy Oil Processing and Utilization, Erickson et al., eds., AOCS, Champaign, 1980. This publication is not provided but is available upon Examiner's request.
Garcia, et al., "Enrichment of butteroil with conjugated linoleic acid via enzymatic interesterification (acidolysis) reactions," Biotechnology letters 20:393 (1998).
McGraw-Hill Encyclopedia of Science and Technology, McGraw-Hill Book Co., N.Y. 1996 (5th ed.). This publication is not provided but is available upon Examiner's request.
Chin, S. F., W. Liu, J. M. Storkson, Y. L. Ha, M. W. Pariza, "Dietary Sources of Conjuagted Dienoic Isomers of Linoleic Acid, a Newly Recognized Class f Anticarcinogens", *J. Food. Comp. Anal.* 5: 185-197 (1992)—published sufficiently before filing date such that the month is not an issue.
Sebedio, J. L., P. Juaneda, G. Dobson, I. Ramilison, J. C. Martin, J. M. Chardigny, W. W. Christie, "Metabolites of Conjugated Isomers of Linoleic Acid (CLA) in the Rat", *Biochem. Biophys. Acta* 1345: 5-10 (1997)—published sufficiently before filing date such that the month is not a issue.
Clement, I., "Review of the Effects of Trans Fatty Acids, Oleic Acid, n-3 Polyunsaturated Fatty Acids, and Conjugated Linoleic Acid on Mammary Carcinogenesis in Animals", *Am. J. Clin. Nutr.* 66 (Suppl.): 1523S-9S (1997)—published sufficiently before filing date such that the month is not an issue.
Sebédio, J. L., A. Grandgirard, and J. Prevost, "Linoleic Acid Isomers in Heat Treated Sunflower Oils", *JAOCS* 65(3): 362-366 (1988)—published sufficiently before filing date such that the month is not an issue.

Holman, R. T., F. Pusch, B. Svingen, H. J. Dutton, "Unusual Isomeric Polyunsaturated Fatty Acids In Liver Phospholipids of Rats Fed Hydrogenated Oil", *PNAS* 88: 4830-34 (1991)—published sufficiently before filing date such that the month is not an issue.
Bradley, T. F., and D. Richardson, "Alkali-Induced Isomerization of Drying Oils and Fatty Acids", *Ind. Eng. Chem.* 34(2): 237-42 (1942)—published sufficiently before filing date such that the month is not an issue.
Radlove, S. B., H. M. Teeter, W. H. Bond, J. C. Cowan, and J. P. Kass, "Catalytic Isomerization of Vegetable Oils", *Ind. Eng. Chem.*, 38(10): 997-1002 (1946)—published sufficiently before filing date such that the month is not an issue.
Cowan, J.C., "Isomerization and Trans-Esterification", *JOACS*, Nov. 1950, p. 492-499 (1950)—published sufficiently before filing date such that month is not an issue.
Belury, M. A., "Conjugated Dienoic Linoleate: A Polyunsaturated Fatty Acid with Unique Chemoprotective Properties", *Nut. Rev.* 53(4): 83-9 (1995)—published sufficiently before filing date such that month is not an issue.
Park, Y., K. J. Albright, W. Liu, J. M. Storkson, M. E. Cook, M. W. Pariza, "Effect of Conjugated Linoleic Acid on Body Composition in Mice", *Lipids* 32(8): 853-58 (1997)—published sufficiently before filing date such that month is not an issue.
Christie, W. W., G. Dobson, F. D. Gunstone, "Isomers in Commercial Samples of Conjugated Linoleic Acid", *JAOCS* 74 (11): 1231 (1997)—published sufficiently before filing date such that month is not an issue.
Lie Ken Jie, M. S. F., M. K. Pasha, M. S. Alam, "Synthesis and Nuclear Magnetic Resonance Properties of All Geometrical Isomers of Conjugated Linoleic Acids", *Lipids* 32 (10): 1041-44 (1997)—published sufficiently before filing date such that month is not an issue.
Sehat, N., M. P. Yurawecz, J. A. G. Roach, M. M. Mossoba, J. K. G. Kramer, Y. Ku, "Silver-Ion High-Performance Liquid Chromatographic Separation and Identification of Conjugated Linoleic Acid Isomers", *Lipids* 33 (2): 217-221 (1998)—published sufficiently before filing date such that month is not an issue.
Lie Ken Jie, M. S. F., J. Mustafa, "High-Resolution Nuclear Magnetic Resonance Spectroscopy—Applications to Fatty Acids and Triacylglycerols", *Lipids* 32 (10): 1019-1037 (1997)—published sufficiently before filing date such that month is not an issue.
Willett, W. C., A. Ascherio, "Trans Fatty Acids: Are the Effects Only Marginal?", *Am J Public Health* 84 (5): 722-24 (1994)—published sufficiently before filing date such that month is not an issue.
Banni et al., J. of Lipid Research 42:1056 (2001).
Chuang et al, Lipids 36:139 (2001).
Bretillon et al., Lipids 34:965 (1999).
Janssen et al., Biomedical and Environmental Mass Spectrometry 16:1-6 (1988).
Park et al., Lipids 34:235-241 (1999).
Sebedio et al., Lipids 34:1319-1325 (1999).
Zambell et al., Lipids 35:777-782 (2000).
Blankson et al., American Society for Nutritional Sciences 1-6 (2000).
Yurawecz et al., Lipid 8:277-282 (1999).

* cited by examiner

CONJUGATED LINOLEIC ACID ALKYL ESTERS IN FEEDSTUFFS AND FOOD

FIELD OF THE INVENTION

This invention relates to the field of nutrition and the supplementation of feedstuffs and food with alkyl esters of conjugated linoleic acid. A process for making the esters utilizes a nonaqueous alcoholate catalyzed reaction to convert the alkyl esters of linoleic acid derived from sunflower and safflower oil to predominately the c9,t11- and t10,c12- conjugated isomers.

BACKGROUND OF THE INVENTION

The biological activity of conjugated linoleic acids (hereinafter CLA) has been well documented in a number of indications. Its effect as an anticarcinogenic agent was demonstrated in a rat mammary tumor model by Ha, et al., Cancer Res., 52: 2035s (1992), and in a mouse forestomach neoplasia model (Ha, et al., Cancer Res., 50: 1097 (1990). CLA has been found effective in attenuating allergic reactions mediated by type I or TgE hypersensitivity. As a nutritive supplement, CLA administration results in selective reduction in body fat, as disclosed in U.S. Pat. No. 5,554,646, and has a significant positive effect on feed conversion efficient as shown in U.S. Pat. No. 5,428,072.

Linoleic acid is an important component of biolipids, and comprises a significant proportion of triglycerides and phospholipids. It is an essential fatty acid, in that it is required in the diet for maintenance of healthy cells, but the body does not possess the enzymatic machinery to synthesis the fatty acid itself. Linoleic acid has 18 carbon atoms with double-bonds at positions 9 and 12. The conjugated forms of linoleic acid have the double bond positions shifted so that the double bond pairs are separated by a single methylene group. The rearrangement of the double bonds of linoleic acid to conjugated positions results in eight possible geometric isomers of 9,11 and 10,12 octadecanoic acid (c9,c11; c9,t11; t9,c11; t9,t11; c10,c12; c10,t12; t10,c12; and t10,t12. Other minor conjugated forms appear in nature and result from synthetic processes, namely, ct8,ct10 and ct11,ctl3 being the most prevalent.

A general mechanism for the isomerization of linoleic acid was described by J. C. Cowan in JAOCS, 72: 492 (1950). It is believed that the double bond is polarized by the result of a collision with an activating catalyst. The polarized carbon atom and its adjoining carbon are then free to rotate and the forces are such to make the deficient carbon atom essentially planar. When the system relieves forces set up as a result of the molecular collision, both cis and trans isomers are formed. More of the 10,12 and 9,11 isomers are formed than other species because of the thermodynamic stability of these forms. More severe conditions of heat, pressure, and polarity tend to drive isomerization further to the more stable trans,trans isomers, and cause redistribution of the double bonds with the appearance of significant quantities of the 8,10 and 11,13 forms.

One problem with aqueous alkali isomerization, which is the principal industrial process for producing CLA, is the formation of these multiple species. The reaction becomes uncontrolled and a significant proportion of the linoleic acid substrate is sacrificed to undesirable trans, trans isomers. For industrial use in drying oils where generalized polymerization between fatty acid strands is sought, it makes little difference which species of conjugated isomer predominate. However, in therapeutic or nutritional applications, the t10, c12 and c9,t11 isomers are believed to contain most, if not all, of the biological activity.

Other methods have been described utilizing metal catalysts, which are not highly efficient. Isomerization in these systems could be achieved more rapidly in the presence of higher molecular weight solvents. Kass, et al., J. Am. Chem. Soc., 61:4829 (1939) showed that replacement of ethanol with ethylene glycol resulted in both an increase in conjugation in less time. U.S. Pat. No. 2,350,583 and British Patent No. 558,881 (1944) achieved conjugation by reacting fatty acid soaps of an oil with an excess of aqueous alkali at 200–230 degrees C. and increased pressure. Among the processes known to cause isomerization in the absence of aqueous alkali, is a nickel-carbon catalytic method, as described in Radlove, et al., Ind. Eng. Chem., 38:997 (1946).

Processes have also been described for isomerization of polyethanoid fatty acids in their ester forms. U.S. Pat. Nos. 2,242,230 and 3,162,658 disclose methods in which the lower alkyl esters of linoleic acid are isomerized by catalysis with basic alcoholates, preferably sodium or potassium at moderate temperatures in the range of 100–140 degrees C. Typically these processes are used to generate industrial drying oils, and hence predominately utilize soy and corn oil is the starting material, in order to enhance polymerization when coated onto surfaces. These fatty acid ester compositions are not suitable for human or animal consumption because of high phosphidyl and other residue content. Purification by distillation, differential extraction, and the like removes the residues, but also causes further double bond rearrangements giving an unacceptable level of trans,trans CLA isomers, and intermolecular polymers.

The purified CLA utilized in prior feeding studies was obtained by small scale laboratory procedures involving production of CLA from highly purified linoleic acid. For example, Sullivan, J. Am. Oil Chemists' Soc., 53:359 (1976) describes a laboratory semi-pilot steam refining system made entirely of glass. While such systems are adequate for producing quantities of CLA for laboratory studies, or even clinical trials, they are not suitable for commercial scale bulk production. On the other hand, the large scale systems available to produce industrial quantities of CLA cannot be run inexpensively enough to produce material for bulk animal feeds. The degumming, refining, and dehydration steps necessary to obtain nutritionally safe edible CLA for livestock feeding are prohibitively complex and expensive.

Economical CLA-ester production in commercial quantities is a desirable objective in light of nutritional benefits observed on a laboratory scale. The advantages of an ester derivative rather than the free CLA fatty acids include resistance to oxidation, ease of manufacture according to the process of the present invention, palatability, and compatibility with lipid feed components.

SUMMARY OF THE INVENTION

In the present invention, a feed safe conjugated linoleic acid alkyl ester is manufactured under conditions preferentially controlling isomerization to the desired 10,12 and 9,11 isomers, while limiting formation of 8,10; 11,13; and trans, trans species. Such conditions are met by employing an alkali alcoholate catalyzed reaction in which a seed oil is split to release free fatty acids from a glycerol backbone and then esterifying prior to isomerization. The key to an adaptation of this process to a commercially viable product is reduction in the process steps which add cost. Typically, residues derived from non-oil components of seed oils, such as sterols and phosphatides, foul equipment and reduce palatability for feed or food use. In the case of typical seed oils such as soy or corn these residues are present in sufficient quantity that a CLA-ester product could not be used in consumable products.

In the composition of the present invention, non-oil residues are not purified away from the oil component, but rather the source of oil is selected to maintain such residues at acceptable levels. By selecting safflower or sunflower oil as an oil source, critical residue levels can be controlled to between 0.1 and 0.5% phosphatides, and to an unsaponifiable sterol fraction containing between 5 and less than 20 percent each of campesterol and stigmasterol, without extensive degumming and distillation processing steps. The resulting linoleic acid alkyl ester is comprised of at least 50 percent up to about 99 percent by weight of octadecanoic acid ester isomers representing combinations of various possible individual percentages of c9,t11-octadecanoic acid alkyl ester and t10,c12-octadecanoic acid alkyl ester. In the alkali alcoholate catalyzed process roughly equal amounts of each of these ester isomers are produced, but the relative percentages can by altered by addition of one or the other of a composition enriched for one isomer. The CLA ester may then be incorporated into an animal feed by compounding the feed from conventional ingredients in a ration typical for the species and age of the animal, and blending therewith the conjugated linoleic acid alkyl esters in a biologically active concentration, generally about 0.05 to 3.5 percent by weight.

The CLA-ester product of the present invention is obtained by direct isomerization of an unrefined linoleic acid, e.g. a linoleic acid source not subjected to refining steps. The CLA-ester composition has one part comprising at least 50 percent by weight of ester isomers (up to substantially 100 percent) of a mixture of ester isomers of c9,t11-octadecanoic acid ester and t10,c12-octadecanoic acid ester, a second part comprising less than about 10 percent by aggregate weight of ester isomers of the structure 8,10-octadecanoic acid ester, 11,13-octadecanoic acid ester, and trans,trans-octadecanoic acid esters, and a third part containing a phosphatidyl residue of between 0.1 and 0.5 percent of the total composition weight. The alkyl groups may be methyl, ethyl, propyl, isopropyl, butyl, isobutyl and the like. Adjustments in concentration of the c9,t11 and t10,c12 isomers can be made by addition of a composition enriched for one or the other isomer to yield an ester composition wherein the c9,t11, or the t10,c12 respectively contained in the first composition part constitutes greater than 60 percent of the total isomers of octadecanoic acid esters.

In the process embodiment of the present invention resulting in a food grade composition suitable for an animal feed, food ingredient, or human dietary supplement, an unrefined CLA-ester having a phosphatidyl residue less than 0.5 percent is treated with an alkali alcoholate in the presence of a monohydric low molecular weight alcohol such as methyl or ethyl alcohol, continuing the treatment at low temperature (about 90 to 145 degrees C.) until at least 50 percent of the ester is converted to CLA-ester, acidifying by addition of an aqueous acid, and then separating the CLA-ester from the aqueous acid without a distillation step.

DETAILED DESCRIPTION OF THE PREFERRED EMBODIMENTS

Various methods of producing conjugated double bonds by alkali isomerization are known in the art. U.S. Pat. No. 2,350,583 (Bradley, 1944) describes a method of producing conjugated fatty acids by aqueous alkali isomerization. This method resulted in the conjugation of about 50% of the double bonds present in the polyunsaturated fatty acids used. U.S. Pat. No. 2,242,230 (Burr et al., 1941) describes a method of non-aqueous alkali conjugation of fatty acids, resulting in the conjugation of approximately 100 percent of the double bonds in the polyunsaturated fatty acids studied. Another process resulting in the efficient formation of conjugated double bonds is described in U.S. Pat. No. 4,381,264 (Struve, 1983). There, the inventors treat polyunsaturated fatty acids with $SO_2$ in the presence of substoichiometric amounts of soap forming bases. Perhaps the most commercially viable method for producing large quantities of conjugated fatty acids is the continuous flow aqueous alkali isomerization process described in U.S. Pat. No. 4,164,505. This process results in essentially all available double bonds being conjugated in a short reaction time. The foregoing patents are incorporated herein by reference.

In the production of a food grade CLA-ester, a laboratory scale procedure utilizes reagent grade 9,12-linoleic acid alkyl ester in a reaction as disclosed in U.S. Pat. Nos. 2,242,230 and 3,162,658, hereby incorporated by reference. The reaction is carried out at about 100–140 degrees C. in a closed vessel for 5–8 hours. Isomerization is substantially complete. The resulting product is perfectly safe for human or animal consumption. However, the use of reagent grade linoleic acid esters is impractical for compounding into bulk feeds, or even for human consumption in capsule form. On the other hand mere isomerization of the linoleic acid contained in a crude or unrefined linoleic ester, as is suitable for production of the industrial drying oils contemplated by the above cited patents, will not yield a food grade because of the high phosphatidyl and sterol content, as well as a tendency for oils containing high levels of these impurities to polymerize.

Applicants have discovered that if sunflower or safflower oil is utilized, the resulting phosphatidyl and sterol residues are low enough for the material to be characterized as food grade. In particular, Applicants first provide the sunflower or safflower oil as delivered by tanker, subject it to fat splitting and esterification, and then proceed directly with the unrefined esterification product into isomerization. The usual purification and refining steps are not necessary. This material can be made in commercial scale quantities at a low enough cost to be practical as a feed or food supplement.

Figure 1:
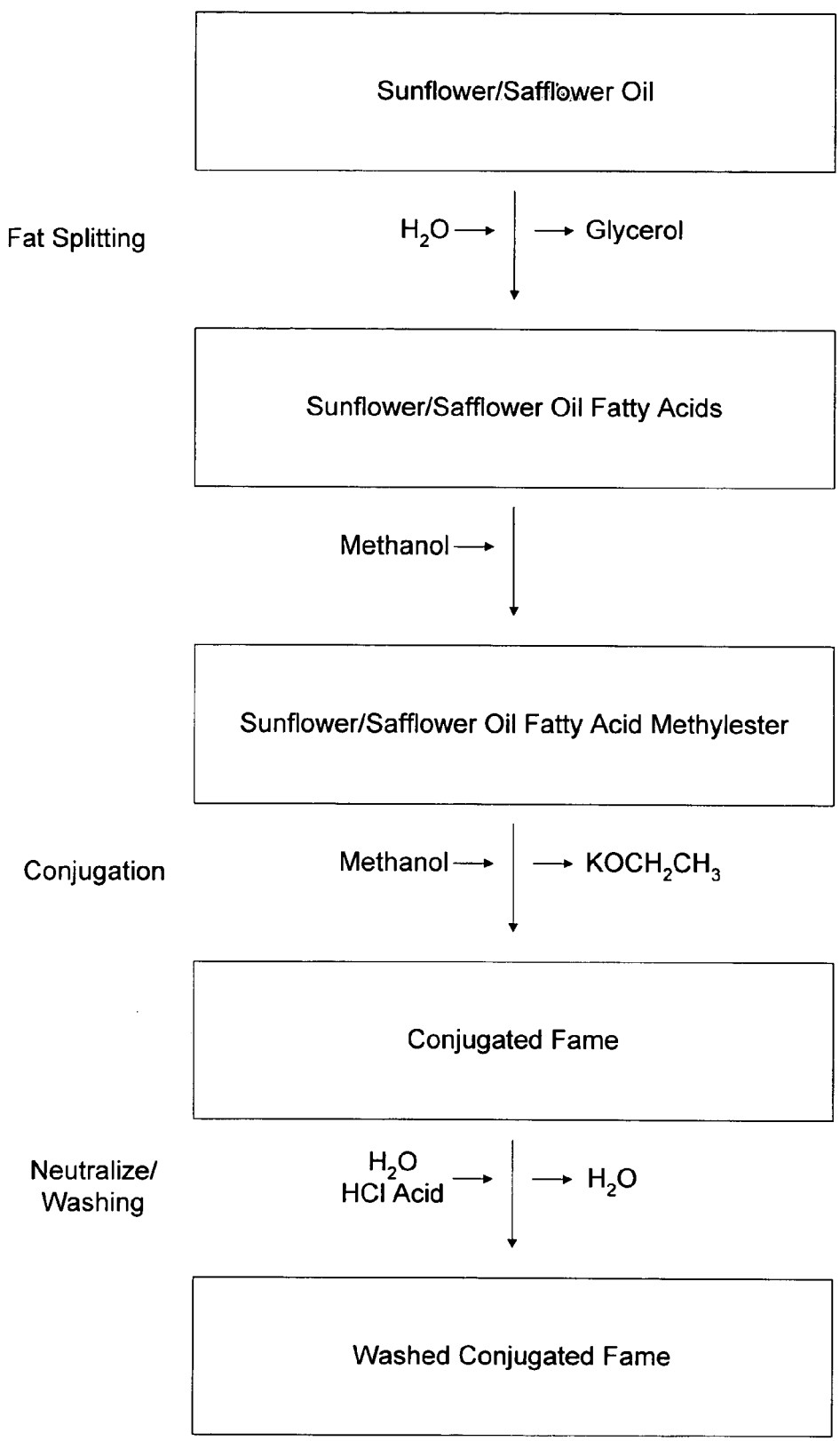
FIG. 1 is a flow diagram of the present process, in which esterification is followed directly by isomerization without a purification step.

Referring now to the flow diagram of FIG. 1, after fat splitting and dehydration, the free fatty acids are combined with methanol or other monohydric low molecular weight alcohol and heated to the temperature at which the alcohol boils. Esterification proceeds under refluxing conditions with removal of the reaction water through a condenser. After the addition of a further quantity of the same or a different monohydric alcohol an alcoholate catalyst is blended into the ester mix. Typical alcoholate catalysts are sodium or potassium ethoxide, or their methyl, butyl, or propyl counterparts.

In the esterification, methanol or ethanol are preferred, although other branched or straight chain monohydric alcohols may be used. The longer the aliphatic chain of the alkyl group, the more lipid compatible the material becomes. Also the viscosity tends to increase. For different types of feed or food, whose consistency varies, product of varying viscosity can be used to obtain the desired flow or compounding characteristics without affecting the therapeutic or nutritional properties arising from the CLA moieties. The theory and practice of esterification are conventional. A basic explanation of the most common methods is set forth in the McCraw-Hill Encyclopedia of Science & Technology, McGraw-Hill Book Co., N.Y.: 1996 (5th ed.). The animal and human body has a variety of esterases, so that the CLA-ester is cleaved to release the free fatty acids readily. Tissue uptake may have a different kinetics depending on the tissue involved and the benefit sought.

In the isomerization step, it was found that alcoholate catalysis produced a much superior product than aqueous alkali mediated isomerization. The latter process always produced undesirable isomers even under mild reaction conditions. The milder conditions do give lower amounts of unwanted isomers, but at the great expense of yield, as shown in the Examples. In most systems the appearance of the c9,t11 and t10,c12 isomers dominates and they are formed in roughly equimolar amounts. It has not heretofore been possible to control the isomerization of the one isomer to the exclusion of the other. While it is desirable to increase the percentage of one or the other isomer (depending on the physiological effect to be achieved), at present this must largely be carried out by adding an enriched source of the desired isomer.

Crude sunflower or safflower oil is the preferred fatty acid source for producing CLA. Sunflower oil contains a high amount of linoleic acid (about 65% on average). Safflower oil typically contains even higher amounts (greater than 70%). Preferably, a hexane extract of crude, non-degummed oil is the starting substrate for CFAP production. This extract is commercially available and is the same quality as the oil used as the starting point for edible products. The ability to use raw sunflower or safflower oil as the starting substrate provides an important economic advantage because it is less expensive than refined sunflower oil.

Applicants have discovered that other raw oils, such as raw corn and soybean oils, are not suited to the present new use of CLA in bulk feeds because of the production of polymerized products during the fat splitting and conjugation processes, and because of the high phosphatide content. Also, certain sterols such, as campesterol and stigmasterol are known to have a tendency to foul processing equipment during conjugation and plug nozzles during materials transfer. The polymerization by-products also result in loss of yield from these other oils, even though at first glance the other oils may seem to have more desirable properties. Corn oil (about 56% linoleic acid) and soybean oil (about 50–55% linoleic acid) have comparable linoleic acid contents as compared to sunflower oil (about 60% linoleic acid). These oils are inexpensive and large quantities are available, which make them attractive candidates as a potential source of CLA for bulk feeds. However; their use for commercial CLA production is substantially lower per unit quantity of oil because the ultimate yields of CLA are lower than for sunflower or safflower oil, and because of the added expense for additional cleaning and purification steps.

Heat sensitive triglycerides containing multiple double bonds are abundant in oils having an iodine value above 120. Oils containing such heat-sensitive triglycerides have a tendency to form polymers when subjected to continuous countercurrent fat-splitting. These polymers become insoluble in oil and will foul equipment, resulting in lowered efficiencies of splitting and yields. Sunflower oils are classified as heat-sensitive because of their high linoleic acid content and iodine number. Sunflower oil has an iodine number of 130; safflower oil of about 145. Soybean oil has an iodine number of about 132, and corn oil has an iodine number of about 130. All these oils have high linoleic acid contents and iodine numbers above 120, thus belonging to the heat-sensitive group. It is therefore surprising that sunflower and especially safflower oils can be split and conjugated by commercial processes with few processing complications.

The prevalent phosphatides are phosphatidylethanolamine, phosphatidyliniositol and phosphatidylcholine. The phosphatide content of sunflower and safflower oils is about 0.4 to 1.0 % as reported in Klein and Crauer, JAOCS 51:382A–385A and Burkhardt, JAOCS 48:697–699 (1971), respectively. In contrast, the phosphatide content of soybean oil is about 1.5–2.5% as reported in the Handbook of Soy Oil Processing and Utilization, Erickson et al. eds., AOCS, Champaign, 1980. For crude oils with low amounts of these substances, such as sunflower and safflower oils, proceeding can advance directly to esterification and isomerization after degumming.

EXAMPLE 1

Effect of Varying Temperature and Reaction Duration on CLA Yield and Composition The effect of temperature and reaction duration on the conjugation of safflower oil was determined. Water and NaOH were added to a high pressure reactor (Parr Model 450 ML Benchtop Alloy 400, equipped with a pressure gauge and stirrer) as indicated in Table 1, columns 1 and 2. The NaOH was allowed to dissolve and safflower oil (column 3) was added to the reactor. The reactor was closed and flushed for 2 min. with nitrogen and then all valves were closed. The reactor was heated in an electrical gasket to the desired temperature (column 4) and maintained at that temperature for the desired time (column 5). The temperature was then reduced to 60° C. before pressure was released and the reactor opened. For each reaction, two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography.

The results of the gas chromatography are presented in column 6 (total percentage of 9,11 and 10,12 isomers), column 7 (total percentage of 11,13 isomers), and column 8 (total percentage of all CLA isomers or yield). These data indicate that as reaction duration and temperature increase, the total amount of conjugation and the percentage of 11,13 isomers increase. Under conditions where formation of the 11,13 isomer is low, the total amount of conjugation is also low.

Figure 2:
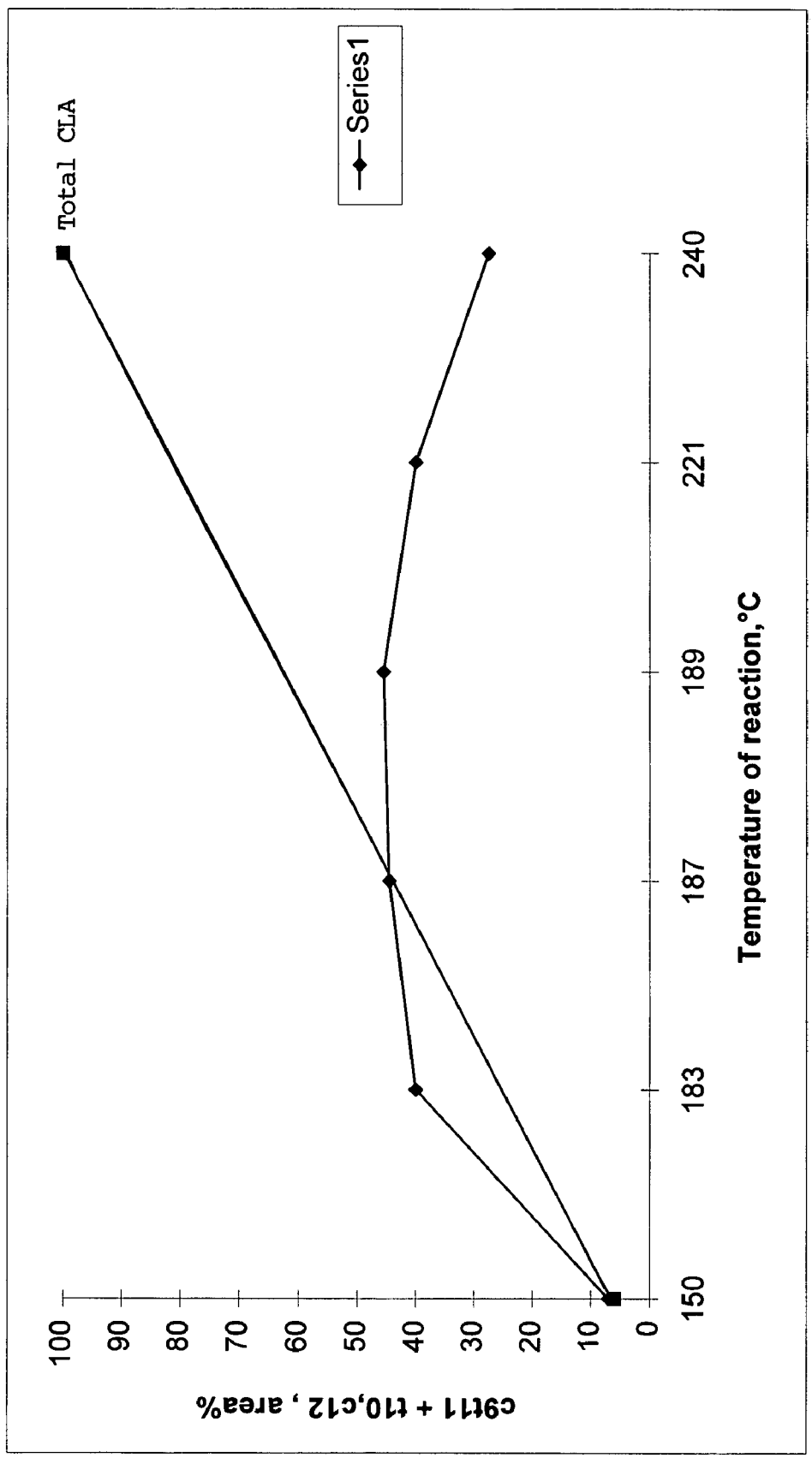
FIG. 2 is a rectilinear plot showing the relation between aqueous alkali processsing temperature and the yield of the 9,11 and 10,12 isomers compared to total conjugated linoleic acids.

FIG. 2 further illustrates the above findings. As temperature is increased, total CLA also increases, but the proportion of the 9,11 and 10,12 isomers declines. At temperatures above 189° C., the absolute amounts of these isomers also declines. The CLA species favored under these conditions are the trans,trans isomers.

TABLE 1

Conjugation in Water Solvent
Summary of Results

| Water gram | NaOH gram | Safflower Oil gram | Mean t. °C. of reaction | Time hours | 9,11+ 10,12 area % | 11,13 area % | CLA total area % |
|---|---|---|---|---|---|---|---|
| 50.21 | 29.93 | 99.94 | 189 | 6.36 | 45.99 | 5.73 | 55.86 |
| 70.20 | 29.93 | 99.94 | 187 | 6.40 | 44.94 | 3.23 | 51.28 |
| 50.10 | 30.17 | 100.74 | 183 | 6.39 | 40.23 | 3.37 | 48.07 |
| 49.91 | 29.93 | 100.40 | 179 | 6.52 | 32.00 | 1.48 | 34.92 |
| 49.97 | 29.80 | 100.02 | 179 | 10.08 | 41.86 | 3.12 | 48.21 |
| 49.94 | 39.84 | 99.84 | 179 | 6.30 | 32.6 | 3.04 | 37.12 |
| 29.50 | 24.83 | 99.21 | 240 | 3.25 | 28.37 | 10.78 | 71.58 |
| 30.33 | 25.15 | 100.43 | 221 | 2.30 | 40.87 | 14.72 | 72.61 |
| 49.92 | 30.00 | 100.36 | 150 | 6.34 | 7.07 | 0 | 7.44 |

EXAMPLE 2

Conjugation of Safflower Fatty Acid Methylester (FAME)

The reaction was carried out in a closed vessel.

The following components were mixed together: 100 g safflower FAME and a mixture of approximately 2.8 g $KOCH_3$ and 2.8 g methanol. There was probably more KOMe than methanol due to evaporation of methanol during mixing of the two components. The mixture was stirred for 5 hours at 111–115 deg C. in nitrogen atmosphere in a closed reaction vessel. The distribution of isomers was analyzed by Gas Chromatography. The results are summarized in Table 2. The raw GC data is presented in Table 3. These data indicate that the conjugation safflower FAME may be accomplished under mild conditions, resulting in a product lacking appreciable amounts of undesirable 8,10 and 11,13 isomers.

TABLE 2

Isomer Distribution

| | |
|---|---|
| Palmitic acid | 6.6% |
| Stearic acid | 2.7% |
| Oleic acid | 12.9% |
| Linoleic acid | 5.7% (unconjugated) |
| CLA c9,t11 | 34.1% |
| CLA t10,c12 | 33.3% |
| CLA c,c | 1.8% |
| CLA t,t | 1.0% |
| CLA total | 70.2% |

EXAMPLE 3

Large Scale Batch Production of Conjugated Safflower FAME

The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of $NaOCH_3$ (30 % solution) were added. The mixture is heated to 65° C. while stirring, and reacted at 65° C. for 2 hours. The resulting bottom layer was decanted while the reactor was purged with nitrogen gas. 1000 liters of water (40–50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour.

To conjugate the safflower FAME, 250 kg of $KOCH_3$ dissolved in methanol to form a paste was added to the reactor. The mixture was then heated to 120° C. while stirring and the reaction allowed to continue for 3 hours. The mixture was cooled to 100° C., and 1000 liters of water (40–50° C., into which 50 kg citric acid monohydrate has been dissolved) was added while stirring. The mixture was stirred for 15 minutes and then the layers were allowed to separate for 20 minutes. The bottom layer was decanted and the product dried at 80° C. for 1 hour and then stored under nitrogen.

The resulting CLA was analyzed using a Perkin Elmer Autosystem XL GC under the following conditions:

| | |
|---|---|
| Column: | WCOT Fused Silica 100 m × 0.25 mm, Coating CP-SIL 88 |
| Carrier: | He gas, 30.0 PSI |
| Temp: | 220 C |
| Run time: | 35–90 min. |
| Inject.: | Splitless, 240 C |
| Detect.: | FID, 280 C |

The GC results are summarized in Table 3.

TABLE 3

Gas Chromatography Results

| Peak # | Time (min) | Component Name | Area (%) | Area (μVs) | Height (μV) |
|---|---|---|---|---|---|
| 1 | 46.874 | C16:0 | 6.37 | 29874.50 | 4026.29 |
| 2 | 58.685 | C18:0 | 2.61 | 12231.70 | 1542.34 |
| 3 | 62.141 | C18:1 c9 | 13.14 | 61668.78 | 7369.08 |
| 4 | 62.652 | | 0.70 | 3263.62 | 391.92 |
| 5 | 66.404 | | 0.35 | 1627.60 | 177.41 |
| 6 | 66.917 | | 0.26 | 1239.15 | 157.35 |
| 7 | 67.583 | C18:2 c9,c12 | 5.75 | 26964.95 | 3153.80 |
| 8 | 70.631 | | 0.25 | 1171.90 | 141.41 |
| 9 | 75.011 | CLA c9,t11 | 34.42 | 161529.90 | 17544.79 |
| 10 | 75.936 | CLA t10,c12 | 33.48 | 157129.82 | 17157.21 |
| 11 | 76.400 | CLA c9,c11 | 0.84 | 3935.70 | 302.61 |
| 12 | 76.631 | CLA C10,c12 | 0.49 | 2316.98 | 279.31 |
| 13 | 77.905 | CLA t,t 9,11 + 10,12 | 1.35 | 6344.50 | 710.88 |
| | | | 100.00 | 469299.10 | 52954.41 |
| 9 | 75.011 | CLA c9,t11 | 48.76 | 161529.90 | 17544.79 |
| 10 | 75.936 | CLA t10,c12 | 47.43 | 157129.82 | 17157.21 |
| 11 | 76.400 | CLA c9,c11 | 1.19 | 3935.70 | 302.61 |
| 12 | 76.631 | CLA c10,c12 | 0.70 | 2316.98 | 279.31 |
| 13 | 77.905 | CLA t,t 9,11 + 10,12 | 1.92 | 6344.50 | 710.88 |
| | | | 100.00 | 331256.90 | 35994.80 |

The following are examples of typical animal rations containing the CLA esters of the present invention.

EXAMPLE 4

PIG STARTER RATIONS

| Ingredients | lbs. | kgs. |
|---|---|---|
| Corn, yellow (8.4% protein) | 1067 | 484.7 |
| Soy bean meal, solvent extracted, dehulled (47% protein) | 570 | 259 |
| CLA-ester | 5 | 2.3 |
| Whey, dried (12.0% protein) | 300 | 136 |
| Dicalcium phosphate | 24 | 11 |
| Limestone | 16 | 7 |
| Iodized salt | 5 | 2 |
| Trace mineral premix | 5 | 2 |
| Vitamin premix | 8 | 4 |
| Totals | 2000 | 908 |

GROWER-FINISHER RATIONS FOR PIGS (FROM 40–240 LBS[18–109 KGS])

| Ingredients | lbs. | kgs. |
|---|---|---|
| Corn, yellow (8.4% protein) | 1566 | |
| Soy bean meal, solvent extracted (44% protein) | 380 | |
| CLA-ester | 5 | |
| Dicalcium phosphate | 21 | |
| Limestone | 15 | |
| Iodized Salt | 5 | |
| Trace Mineral Premix | 3 | |
| Vitamin Premix | 3 | |
| Total | 2000 | |

PIG GROWER FINISHER RATIONS (FOR PIGS 121–240 LBS[55–109 KGS])

| Ingredients | lbs. | kgs. |
|---|---|---|
| Corn, yellow (8.4% protein) | 1687 | |
| Soybean meal, solvent extracted (44% protein) | 265 | |
| CLA-ester | 5 | |
| Dicalcium phosphate | 18 | |
| Limestone | 15 | |
| Iodized salt | 5 | |
| Trace mineral premix | 2 | |
| Vitamin premix | 3 | |
| Total | 2000 | |

COMPOSITION AND ANALYSIS OF PIG TRACE MINERAL REMIX

| Element | Source | Amount (lbs) |
|---|---|---|
| Copper (Co) | Copper Sulfate | 1.500 |
| Iodine (I) | Potassium Iodide | 0.010 |
| Iron (Fe) | Ferrous Sulfate | 25.000 |
| Manganese (Mn) | Manganese Sulfate | 2.500 |
| Selenium (Se) | Sodium Selemite) | 0.025 |
| Zinc (Zn) | Zinc Sulfate | 25.000 |
|  | Carrier | 45.965 |
| Total |  | 100.000 |

COMPOSITION OF PIG VITAMIN PREMIX

| Vitamins | Amount |
|---|---|
| Essential | |
| Vitamin A (million IU) | 5.0 |
| Vitamin D (million IU) | 0.6 |
| Vitamin E (thousand IU) | 26.0 |
| Niacin (g) | 25.0 |
| d-Pantothenic acid (g) | 20.0 |
| Riboflavin (g) | 6.0 |
| Vitamin B-12 (mg) | 25.0 |
| Optional | |
| Biotin (g) | 0.3 |
| Menadione (g) | 4.0 |
| Carrier | to 10 lbs |
| Total | 10.0 |

18% PROTEIN LAYER RATIONS FOR HENS

| Ingredients | lbs. | kgs. |
|---|---|---|
| Ground yellow corn | 1242 | 564.5 |
| CLA-ester | 5 | 2.3 |
| Alfalfa meal, 17% | 25 | 11.3 |
| Soybean meal, dehulled | 451.6 | 205.3 |
| Meat and bone meal (47%) | 50 | 23.0 |
| DL-methionine | 1.0 | .5 |
| Dicalcium phosphate | 7 | 3.1 |
| Ground limestone | 174 | 79.1 |
| Iodized salt | 7 | 3.1 |
| Stabilized yellow grease | 37 | 17.2 |
| Mineral and vitamin supplements | | |
| Calcium pantothenate (mg) | 5,000 | |
| Manganese (g) | 52 | |
| Selenium (mg) | 90.8 | |
| Zinc (g) | 16 | |
| Vitamin A (IU) | 6,000,000 | |
| Vitamin $D_3$ (IU) | 2,000,000 | |
| Choline (mg) | 274,000 | |
| Niacin (mg) | 12,000 | |
| Riboflavin (mg) | 2,000 | |
| Vitamin B-12 | 6 | |
| Total | 2000 | 909.4 |

STARTER AND FINISHER RATIONS FOR BROILERS

| Ingredients | Starter (up to 24 days) lbs. | kgs. | Finisher (25 days to market) lbs. | kgs. |
|---|---|---|---|---|
| Ground yellow corn | 1,106 | 503 | 1235 | 561 |
| CLA-ester | 5 | 2.3 | 5 | 2.3 |
| Soybean meal, dehulled | 605 | 275 | 420 | 191 |
| Alfalfa meal, 17% | — | — | 25 | 11 |
| Corn gluten meal, 60% | 50 | 23 | 75 | 34 |
| Fish meal, herring, 65% | 50 | 23 | 50 | 23 |
| Meat and bone meal, 47% | 50 | 23 | 50 | 23 |
| Dicalcium phosphate | 10 | 4 | 9 | 4 |
| Ground limestone | 16 | 7 | 14 | 6.3 |
| DL-methionine | 0.8 | 0.3 | — | — |
| Stabilized yellow grease | 101 | 45.7 | 110 | 49.4 |
| Iodized salt | 7 | 3 | 7 | 3 |
| Mineral and vitamin supplement | | | | |
| Calcium pantothenate (mg) | 5,000 | | 5,000 | |
| Manganese (g) | 75 | | 75 | |
| Organic arsenical supplement | 0.1 | | 0.1 | |
| Selenium (mg) | 90.8 | | 90.8 | |
| Zinc (g) | 30 | | 30 | |
| Vitamin A (IU) | 4,000,000 | | 4,000,000 | |
| Vitamin D (IU) | 1,000,000 | | 1,000,000 | |
| Vitamin E (mg) | 2,000 | | 2,000 | |
| Vitamin K (mg) | 2,000 | | 2,000 | |
| Choline (mg) | 503,000 | | 672,000 | |
| Niacin (mg) | 20,000 | | 20,000 | |
| Riboflavin (mg) | 3,000 | | 3,000 | |
| Vitamin B-12 (mg) | 12 | | 12 | |
| Total | | 2000.9 | 909.3 | 2000.1 | 909.5 |

GROWER/FINISHER TURKEY RATIONS

| Ingredients | Grower (8–16 weeks) lbs. | kgs. | Finisher (16 weeks-market) lbs. | kgs. |
|---|---|---|---|---|
| Ground yellow corn | 1194 | 595 | 1490 | 677.2 |
| Wheat middlings | 50 | 23 | — | — |
| Alfalfa meal, 17% | 25 | 11.3 | 25 | 11.3 |
| Soybean meal, dehulled | 570 | 259 | 335 | 152.3 |
| Meat and bone meal, 47% | 50 | 23 | 50 | 23 |
| Dicalcium phosphate | 32 | 14.5 | 23 | 10.5 |
| Ground limestone | 14 | 6 | 17 | 8 |
| Stabilized yellow grease | 45 | 20.7 | 45 | 20.7 |
| CLA-ester | 5 | 2.3 | 5 | 2.3 |
| Iodized Salt | 10 | 4.5 | 10 | 4.5 |
| Mineral and vitamin supplements | | | | |
| Calcium pantothenate (mg) | 4,500 | | 4,500 | |
| Manganese (g) | 30 | | 30 | |
| Selenium (mg) | 181.6 | | 181.6 | |
| Zinc (g) | 30 | | 30 | |
| Vitamin (IU) | 1,500,000 | | 7,500,000 | |
| Vitamin D (IU) | 1,700,000 | | 1,700,000 | |
| Vitamin E (IU) | 10,000 | | 10,000 | |
| Biotin (mg) | 100 | | 100 | |
| Choline (mg) | 388,000 | | 417,000 | |
| Niacin (mg) | 46,000 | | 48,000 | |
| Riboflavin (mg) | 5,000 | | 5,000 | |
| Vitamin B-12 | 6 | | 6 | |
| Total | | 2000 | 909.3 | 2000 | 909.3 |

DRY DOG FOOD FORMULA

| Ingredients | Formula 1, % | Formula 2, % |
|---|---|---|
| Meat and bone meal, 50% CP | 8.0 | 15.0 |
| Fish meal, 60% CP, low fat | 5.0 | 3.0 |
| Soybean meal, 44% CP | 12.0 | — |
| Soybean meal, 50% CP | — | 19.0 |
| Wheat germ meal, 25% CP | 8.0 | 5.0 |
| Skimmed milk, dried | 4.0 | 2.75 |
| Cereal grains, mixed | 51.23 | — |
| Corn, flaked | — | 23.25 |
| Wheat bran | 4.0 | — |
| Wheat, flaked | — | 23.35 |
| Animal fat | 1.75 | 2.75 |
| CLA-ester | .25 | .25 |
| Steamed bone meal | 2.0 | — |
| Brewers yeast | 2.0 | 5.0 |
| Fermentation solubles, dehydrated | 1.0 | — |
| Salt and trace minerals | 0.5 | 0.5 |
| Vitamin mixture | 0.25 | 0.25 |
| Ferric oxide | 0.02 | — |
| Total | 100.00 | 100.00 |

SEMI-MOIST DOG FOOD FORMULAS

| Ingredients | Formula 1, % | Formula 2, % |
|---|---|---|
| Soy flakes | 30.9 | 33.5 |
| Meat byproducts, 70% moisture | 32.0 | — |
| Meat and bone meal, dehydrated | — | 7.3 |
| Water | — | 25.6 |
| Sugar | 21.0 | 21.0 |
| Calcium and phosphorous supplement | 3.3 | — |
| Soybean hulls | 3.1 | 3.1 |
| Skimmed milk, dried | 2.5 | — |
| Propylene glycol | 2.1 | 2.1 |
| Sorbitol | 2.0 | 2.0 |
| Animal fat | .75 | 3.95 |
| CLA-ester | .25 | .25 |
| Emulsifiers | 0.9 | — |
| Potassium sorbate | 0.35 | 0.35 |

-continued

SEMI-MOIST DOG FOOD FORMULAS

| Ingredients | Formula 1, % | Formula 2, % |
|---|---|---|
| Salt | 0.6 | 0.6 |
| Vitamins | 0.25 | 0.25 |
| Total | 100.000 | 100.000 |

What is claimed is:

1. A food product comprising conjugated linoleic acid alkyl esters in a biologically active concentration, said alkyl esters comprising less than about two percent trans,trans; 8,10 and 11,13 octadecadienoic acid isomers.

2. The food product of claim 1 wherein the concentration of conjugated linoleic acid alkyl esters in said food product is about 0.05 to 3.5 percent by weight.

3. The food product of claim 1 wherein said conjugated linoleic acid alkyl ester is comprised of at least 50 percent up to about 99 percent by weight of octadecadienoic acid alkyl ester isomers selected from the group consisting of c9,t11-octadecadienoic acid alkyl ester and t10,c12-octadecadienoic acid alkyl ester.

4. A conjugated linoleic acid alkyl ester composition for safe use as a feed, food ingredient, or food supplement obtained by direct isomerization of an unrefined linoleic acid comprising a composition of isomers in one part comprising at least 50 percent by weight of ester isomers selected from the group consisting of c9,t11-octadecadienoic acid alkyl ester and t10,c12-octadecadienoic acid alkyl ester, and combinations thereof, and in a second part comprising less than two percent by aggregate weight of ester isomers selected from the group consisting of 8,10-octadecadienoic acid alkyl esters, 11,13-octadecadienoic acid alkyl esters, and trans,trans-octadecadienoic acid alkyl esters, and in a third part comprising in the range of 0.1 to 0.5 percent phosphatidyl residue remaining after isomerization of said unrefined linoleic acid.

5. The ester composition of claim 4 wherein said c9,t11-octadecadienoic acid alkyl ester contained in said first composition part constitutes greater than 60 percent of the total isomers of octadecadienoic acid alkyl esters.

6. The ester composition of claim 4 wherein said t10,c12-octadecadienoic acid alkyl ester contained in said first composition part constitutes greater than 60 percent of the total isomers of octadecadienoic acid alkyl esters.

7. The food product of claim 1 wherein said conjugated linoleic acid alkyl esters have an alkyl radical selected from the group consisting of methyl-, ethyl-, propyl-, isopropyl-, butyl-, and isobutyl-.

* * * * *